United States Patent [19]

Crevoiserat

[11] Patent Number: 4,592,825
[45] Date of Patent: Jun. 3, 1986

[54] PROBE FOR MEASURING OXYGEN PARTIAL PRESSURE IN A GAS ATMOSPHERE

[76] Inventor: Térésa Crevoiserat, 2944 Bonfol, Switzerland

[21] Appl. No.: 768,182

[22] Filed: Aug. 23, 1985

Related U.S. Application Data

[63] Continuation of Ser. No. 573,314, Jan. 24, 1984, abandoned.

[30] Foreign Application Priority Data

Feb. 4, 1983 [CH] Switzerland ............................ 652/83

[51] Int. Cl.⁴ ............................................ G01N 27/46
[52] U.S. Cl. .................................. 204/426; 204/427; 204/428
[58] Field of Search ................................ 204/421–429

[56] References Cited

U.S. PATENT DOCUMENTS

| 3,454,486 | 7/1969 | Davies | 204/427 |
| 4,040,930 | 8/1977 | Dillon | 204/429 |
| 4,186,072 | 1/1980 | Blumenthal et al. | 204/428 |
| 4,305,803 | 12/1981 | Beyer et al. | 204/429 |
| 4,419,212 | 12/1983 | Dietz et al. | 204/426 |

FOREIGN PATENT DOCUMENTS

| 0006989 | 3/1976 | European Pat. Off. | |
| 2703689 | 8/1978 | Fed. Rep. of Germany | 204/428 |
| 2837680 | 3/1980 | Fed. Rep. of Germany | |
| 3025670 | 3/1981 | Fed. Rep. of Germany | |
| 2938179 | 4/1981 | Fed. Rep. of Germany | |
| 2173564 | 10/1973 | France | |
| 2214128 | 8/1974 | France | |
| 2340548 | 2/1975 | France | |

OTHER PUBLICATIONS

Figure 2:
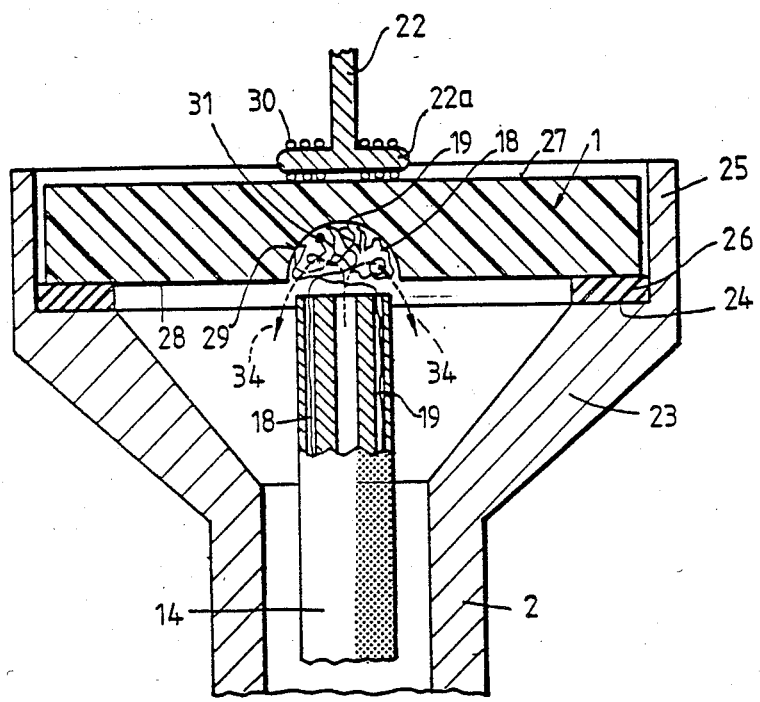

Horsley "AERE Report R-3427", 1961, p. 3 & FIG. 2.
Braunshtein, D., et al., "A Sample Holder for Fuel Cell Measurements at High Temperature," J. Phys. E: Sci. Instrum., vol. 12, No. 10, 10/79, pp. 921–922.

Primary Examiner—T. Tung
Attorney, Agent, or Firm—Parkhurst & Oliff

[57] ABSTRACT

The probe comprises an outer casing communicating through apertures with the atmosphere of a furnace and bearing a support part on which the measuring electrode, or anode, is wound. A tablet of solid electrolyte in contact with the anode can be easily and quickly replaced when the measuring face thereof has become contaminated by the furnace atmosphere. The reference electrode, or cathode, is formed by the soldered junction and one of the wires of a thermocouple, the two conductors of which are crumpled into a hollow in the reference face of the tablet, then pass through a conduit of insulating refractory material. Between the bottom of the casing and that of a tubular support accommodated therein there is a spring which has the effect of pressing the tablet against a washer via the supporting part, thus sealing the furnace atmosphere from a reference atmosphere. The reference atmosphere is maintained by a flow of air or oxygen injected into the conduit and sweeping the wires of the thermocouple, exiting again within the tubular support.

14 Claims, 2 Drawing Figures

PROBE FOR MEASURING OXYGEN PARTIAL PRESSURE IN A GAS ATMOSPHERE

This is a continuation of application Ser. No. 573,314 filed Jan. 24, 1984, now abandoned.

This invention relates to apparatus for pressure measurement, and in particular to a probe for measuring the oxygen partial pressure in a gas atmosphere as compared with a reference atmosphere, of the type comprising a tablet of solid electrolyte disposed in a measuring head at one end of the probe, a tubular support bearing the tablet and separating the gas atmosphere from the reference atmosphere, and measuring and reference electrodes, each in contact with one of the faces of the tablet.

Probes of this kind are used especially for checking the atmosphere of furnaces in which heat treatments are carried out, e.g., cementation treatments. The solid electrolyte tablet is generally a cylindrical piece of zirconium oxide sintered and stabilized by means of yttrium oxide. However, other materials have also been proposed for making these tablets, and probes of the type initially mentioned are also used for determining the ratio of carbon monoxide to carbon dioxide in the atmosphere of the furnace, for example, or for still other types of measurement.

Experience has shown that numerous difficulties are encountered in producing probes capable of giving an accurate measurement of the quantity of oxygen present in the atmosphere of the furnace.

One of the main difficulties encountered, especially with probes intended for heat-treatment furnaces, is due to the fact that the part of the probe situated inside the furnace must operate at temperatures on the order of 900°–1100° C. Moreover, it is in this temperature range that it becomes possible to obtain a potential difference between the two electrodes, which constitutes an accurate measurement of the respective oxygen contents of the two atmospheres.

Another difficulty derives from the fact that it is essential to maintain strict fluid-tightness between the atmosphere to be measured and the reference atmosphere so that the latter will not be polluted by the former.

A third difficulty is presented by the short service life of the zirconium tablets exposed to the furnace atmospheres.

Very often, furnace atmospheres intended for heat treatments are polluted by active vapors or fumes coming from salt residues on the charge material, for example, or by vapors coming from oil-hardening, burnt oil, protective paste, etc.

Such undesirable active vapors or fumes cause various problems in all the present measurement systems ($CO$, $CO_2$, dew point, etc.) and also for oxygen probes, for they irreversibly alter the stabilized zirconium oxide.

The service life of an oxygen probe in a furnace atmosphere where the conditions are particularly severe is very variable. Under ideal conditions (no hardening salt, no vibrations, no oil vapors, atmosphere totally rid of nitrogen before introduction of the new batch, thorough washing of the parts and the charge material), the probes available on the European market last more than a year; but such cases are rare, and 60% of the time the service life is from six weeks to six months.

In most of the prior art probes, e.g., those described in German Disclosed Application (DOS) No. 30 25 670, a tablet of zirconium is sealed by means of a ring or by hot-driving inside a support tube of insulating material. This support tube must have a thermal dilation coefficient as close as possible to that of the sintered zirconium oxide, thus requiring for this tube the use of materials which are also very expensive. The rapid deterioration of the tablet therefore entails the replacement at regular intervals not only of the tablet itself but of the support tube as well, i.e., the most expensive components of the probe.

Another probe of the type initially mentioned is described in French Pat. No. 2,173,564. However, in this prior art design, the measuring and reference electrodes are situated at the periphery of the tablet and take the form of platinum rings. In order to improve the pick-up of the measurement potential, the aforementioned French patent indicates that the measurement face of the tablet may be covered with a porous layer of platinum; but experience has shown that although this solution may be suitable for determining the oxygen content of the exhaust gases of an engine or the fumes of a heating installation, it is not suitable for applications where the probe must operate at temperatures on the order of 1000° C., e.g., for checking the atmosphere of furnaces used for the treatment of metals or other materials. The same drawback is encountered with the probes described in German Published Applications (DOS) Nos. 28 37 680 and 29 38 179 and in other prior disclosures.

It is an object of this invention to provide an improved probe which can be utilized in furnaces operating at high temperatures, one which uses zirconium oxide tablets of a simple shape that are easily replaceable and are held in place under conditions such that an accurate measurement is obtained during the entire life of the tablet.

To this end, in the probe according to the present invention, of the type initially mentioned, the measuring electrode is a metal part provided with projections which press against a central zone of the face of the tablet exposed to the gas, the reference electrode is a metal part which is in contact with the tablet at a plurality of locations on the face thereof exposed to the reference atmosphere, and the fluid-tightness between the two atmospheres is achieved by pressure of the tablet bearing against an annular seat of the tubular support, the bearing force being transmitted by the measuring electrode.

With this design, the tablet is held in place by simple pressure so that it can be replaced very easily and very quickly.

Figure 1:
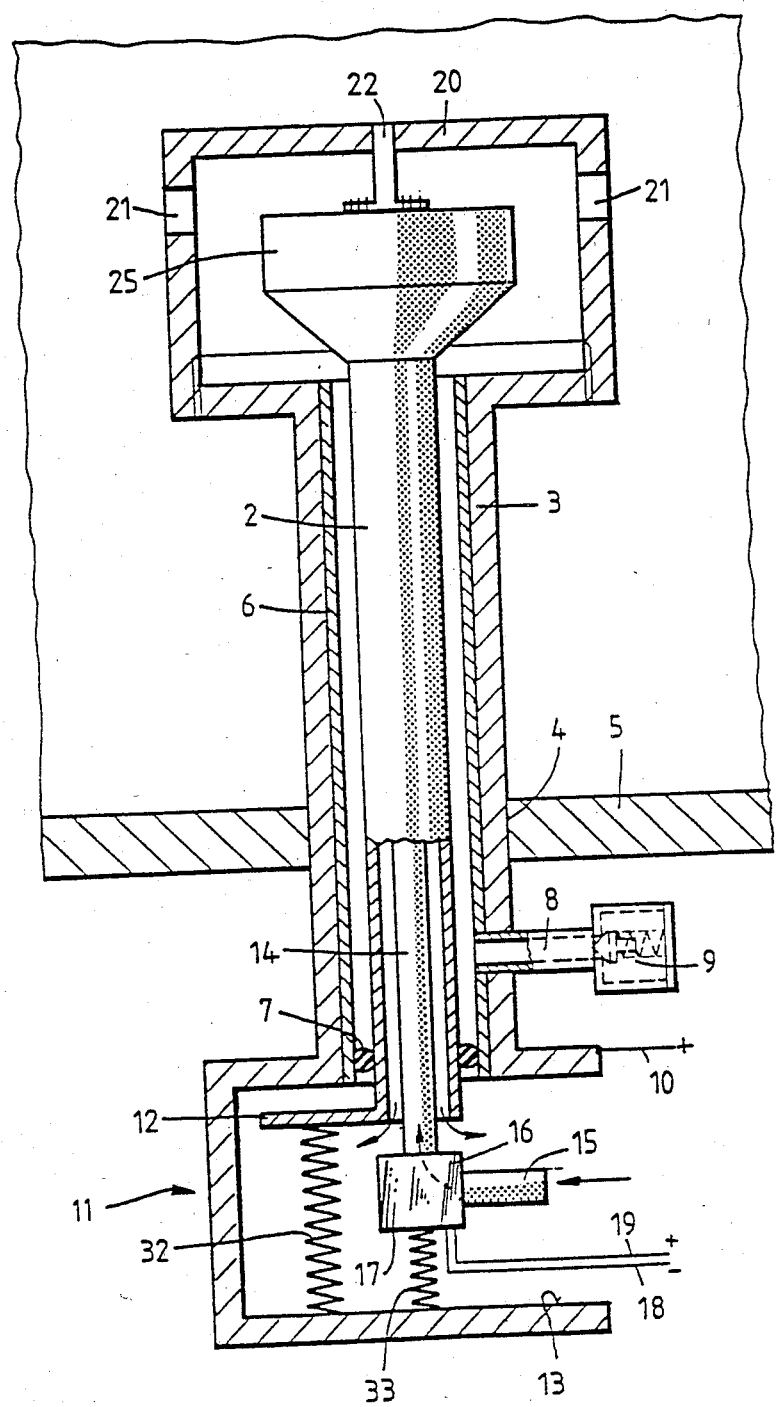

A preferred embodiment of the invention will now be described in detail with reference to the accompanying drawings, in which:

FIG. 1 is a diagrammatic sectional view of the probe, shown in place in a furnace, and FIG. 2 is a partial axial section on a larger scale, showing the measuring element proper.

The drawings illustrate a tablet 1 (FIG. 2) of zirconium oxide, sintered and stabilized with yttrium, and borne by a tubular support 2, the straight middle portion of which is of refractory steel or, as the case may be, of the nickel-chromium-iron alloy sold under the trademark "Inconel." Tubular support 2 is fitted in a second tube 3 (FIG. 1) which forms a casing and passes through an aperture 4 in a wall 5 of a furnace. The overall length of the probe may be on the order of from 70 cm to 1 meter, the end situated inside the furnace constituting a measuring head, while the other end, which remains outside the furnace and is consequently at ambient temperature, bears the means of access to the interior of the probe, as well as the connections to various elements of the measuring instruments. It will be noted here that tube 3 of the casing is also preferably made of refractory steel or of the aforementioned "Inconel" alloy and that it is lined with a layer 6 of platinum. Between tubular support 2 and tube 3 of the casing, a gasket 7, e.g., a rubber toroid of the O-ring type, is disposed at the outer end of the probe.

Before turning to a detailed description of the measuring head, particulars of the elements situated outside the furnace will be given, i.e., those at the end of the probe opposite the measuring head. First, casing 3 bears a coupling 8 with a valve 9. As will be seen below, valve 9 is used for continuously withdrawing samples of the gas constituting the furnace atmosphere to be analyzed for checking purposes or for determining their dew point.

A wire 10 connected to the end of the casing supplies the potential of the measuring electrode to measuring apparatus (not shown).

The outer end of the casing is designed as a sort of cylindrical housing 11 containing various elements, some of which are to be mentioned below.

Within housing 11, tubular support 2 of refractory steel comprises a shoulder flange 12 so disposed that access to the inside of support 2 is possible through an opening 13 of housing 11.

A third tube 14 of insulating material, e.g., ceramics, is accommodated within support 2. Tube 14 extends along the axis of the probe. As will be apparent from the sectional detail depicted in FIG. 2, tube 14 has three parallel passages, one in the center and the other two directly opposite one another. As a modification, it would also be possible to use a ceramic tube provided with four ducts distributed about the axis of the tube.

Returning to FIG. 1, it will be seen that at the opposite end of tube 14 from the measuring head, this tube communicates laterally with a connection pipe 15 through a cylindrical case 16 closed top and bottom, as viewed in the drawing, by flat walls 17. Coming out of case 16 are two wires 18 and 19 which are the two conductive elements of a thermocouple, preferably a thermocouple of the platinum and platinum-rhodium type (with 13% rhodium), these two conductors leading to the measuring apparatus. By means of connection pipe 15, a reference gas, to be described below, is caused to enter tube 14, while this same reference gas can be withdrawn through an outlet between tube 14 and tubular support 2.

The measuring head proper comprises a cap 20 of the aforementioned "Inconel" alloy. Cap 20 is shown diagrammatically in FIG. 1 and is fixed, e.g., by screwing, to the inner end of refractory steel tube 3 of the casing. Cap 20 includes holes 21 at the sides to allow communication between the inside of the casing and the atmosphere of the furnace. At the top of cap 20, which is shown as a flat wall in FIG. 1 but which may preferably be conical, there is an opening into which a support part 22 is screwed, i.e., a rod of the mentioned "Inconel" alloy, the inner end of which takes the shape of a disk or an elongated plate 22a (FIG. 2) disposed perpendicular to the axis of the casing.

FIG. 2 also shows tube 14 and the measuring head end of refractory steel support 2, which tapers into a frustoconical collar 23 bounded at the top, as viewed in the drawing, by a flat shoulder 24 and a thin sidewall 25. Fitted on shoulder 24 is an annular platinum washer 26 of rectangular cross-section, both faces of which are carefully ground and which constitutes a gasket. Zirconium tablet 1 rests upon washer 26. It is cylindrical, not very thick, and has a plane face 27 directed toward the inside of the furnace, this being the measuring face, and an opposite face 28, parallel to face 27, constituting the reference face. The outside diameter of tablet 1 may, for instance, be 24 mm and its thickness 4 mm, these dimensions being given only by way of example. In the center of reference face 28 is a hollow 29 having a hemispherical bottom and cylindrical sides, the dimensions of which are such that the bottom of hollow 29 is situated about 1.5 mm away from measuring face 27, for example. The tablet thus produced is of compact size and consequently possesses high resistance to compression and to bending even at high temperatures. Moreover, the distance between the measuring face and the reference face can be reduced to a very considerable extent, which increases the precision of the measurement as will be seen below.

In this embodiment, a measuring electrode 30 takes the form of a platinum wire which preferably is wound around crosspiece 22a of support part 22. This platinum wire may be from 0.5 to 0.6 mm in diameter, for example. Such an arrangement of the measuring electrode is not the only possible one, however. Thus, the measuring electrode proper could be formed by designing support part 22 as a platinum stud fixed to cap 20; the surface of this stud facing tablet 1 would be milled in such a way that a network of narrow ribs (0.5–0.6 mm, wide) projects from that surface and rests against the center area of measuring face 27. As a matter of fact, it has been found that what is essential is for the platinum measuring electrode to have numerous projecting portions in contact with measuring face 27, but allowing the atmosphere of the furnace to circulate between them, so that there is good contact between the three phases which are present together, viz., the atmosphere of the furnace, the measuring electrode, and the measuring face of the tablet.

On the other side of tablet 1, i.e., reference face 28, the reference electrode is made up of the ends of the platinum and platinum-rhodium wires 18 and 19 which are soldered together at a junction 31 so as to constitute the temperature-measuring thermocouple. Furthermore, the end portions of wires 18 and 19 are twisted back and crumpled up in such a way as to be accommodated within hollow 29, wires 18 and 19 being in contact with the inside surface of hollow 29 at a large number of points. As may be seen, wires 18 and 19 are led through two of the ducts existing within tube 14, so that the crumpled ball of wire forming the reference electrode can be guided and positioned within hollow 29 with the required precision during assembly. Experiments have demonstrated that it is not necessary for all the points of contact between wires 18 and 19 and reference face 28 of tablet 1 to be on the inside surface of hollow 29. Good measuring results have likewise been obtained by making hollow 29 just big enough to contain the soldered junction 31 between wires 18 and 19 and consequently to constitute the temperature-measuring point, while the potential from reference face 28 of solid electrolyte 1 is picked up at points of contact distributed over the plane rear face of tablet 1.

Returning now to FIG. 1, a pressure member diagrammed as a spring 32 will be seen to act between the bottom of housing 11 of the casing and flange 12 of tubular support 2. This pressure member may be so regulated as to exert a predetermined force between components 2 and 3 of the measuring head; and the reaction to this force is seen to be a bearing force which is exerted through support part 22 upon tablet 1, at the center of measuring face 27, the reaction to this force being exerted by washer 26, situated at the periphery of tablet 1. Tablet 1 is thus held in place by bearing forces which exert a bending stress upon it. In order to remove tablet 1 and replace it, it suffices to take the probe out of the furnace and unscrew cap 20. Experience has shown that in a reduction to practice, the arrangement depicted in the drawing offers complete fluid-tightness at the location of washer 26 between the furnace atmosphere prevailing within the housing and the reference atmosphere prevailing within tubular support 2. The optimum bearing force exerted at the center of tablet 1 may differ according to whether the measuring electrode is equipped with a platinum wire such as wire 30 or has a network of milled ribs. In the former case, good results were obtained with a force of 2 kg, whereas in the latter case the force was 7 kg.

FIG. 1 also shows diagrammatically a pressure member 33, which may also be a spring, acting between the bottom of housing 11 and the bottom wall 17 of case 16 integral with tube 14. This force therefore represents that with which the thermocouple (wires 18 and 19), in particular its soldered junction 31, is pressed against the inside surface of hollow 29 to produce the multiple contact between the reference electrode and solid electrolyte tablet 1. In order to pick up the reference potential and measure the temperature correctly, the force of spring 33 will be from 0.1 to 1 kg., for example.

It is important to emphasize that the replaceable zirconium oxide tablets have plane opposite faces which are machined but are not coated. The plane measuring face is preferably roughly milled while the reference face is finely ground.

Moreover, contrary to consistent practice in measuring probes, the zirconium oxide of the tablets does not contain any ferric oxide.

When the probe described above is in actual use, the reference atmosphere is, of course, air. To maintain the stable composition of this reference atmosphere, air is continuously injected through connection pipe 15 and the center duct of tube 14. This flow of air, indicated by arrows 34 in FIG. 2, is under pressure very slightly higher than that prevailing in the atmosphere of the furnace. Thus, not only is the reference electrode constantly swept by a reference atmosphere of the desired standard composition, but what is more, this flow of air carries off toward the outlet any leaks which might still exist at the location of washer 26.

This probe is to be used in conjunction with electronic apparatus comprising the instruments necessary for converting the potential difference measured between wires 18 and 19 to obtain the temperature, and for converting the potential difference measured between connections 19 and 10, i.e., between the platinum electrode of the thermocouple constituting the cathode of the measuring transmitter and wire 10 which is connected by the casing to support part 22 and constitutes the anode of this electrolytic measuring cell.

It will be noted that the probe described above makes possible not only quick and simple replacement of solid electrolyte tablet 1 but also replacement of measuring electrode 30 and support part 22, for these parts can be fixed to cap 20, e.g., by screwing, so that they, too, are easy to change.

The experiments made show that the measurement curves prove excellent measuring sensitivity for carbon contents between 0.2% and 1.2% at 950° C. and between 0.2% and 1.05% at 850° C. The correction factor to be adopted is on the order of 2. As is well known, this correction factor relates to the calculation to be made for taking into account the influence of the temperature and the $CO-CO_2$ ratio on the oxygen partial pressure.

Although platinum and platinum-rhodium electrodes have been described above, other metals may obviously equally well be used for these elements of the measuring device described. In particular, platinum and gold could be used. Moreover, whereas air has been spoken of as constituting the reference atmosphere, it will be clear that this atmosphere might consist of pure oxygen or of a mixture of oxygen and any other gas instead. It will be noted that the inner part of the casing occupied by the furnace atmosphere is sealed from the outside by means of rubber gasket 7 which, of course, works at the ambient temperature. The advantage of using a rubber gasket at this location is that this gasket makes it possible to compensate for the slight variations in position resulting from the action of pressure member 32 (FIG. 1) acting between tubular support 2 and casing 3. However, instead of a pressure member in the form of a spring 32, any other device might just as well be used which is capable of creating between the two components supporting the electrodes, i.e., support 2 and casing 3, the compressive force necessary to ensure the fluid-tightness of the solid electrolyte tablet. Thus, for example, a jack or any other pneumatic, hydraulic, or if need be, electromagnetic device might be used.

What is claimed is:

1. A probe for measuring the oxygen partial pressure in a gaseous atmosphere as compared with a reference atmosphere, comprising:

a tablet of solid electrolyte having a first face exposed to the gaseous atmosphere and a second face exposed to the reference atmosphere;

a tubular support releasably bearing against said tablet and separating said gaseous atmosphere from said reference atmosphere;

a measuring electrode in contact with a central zone of said first face of said tablet;

a reference electrode in contact with a central zone of said second face of said tablet;

an annular seat surface at one end of said tubular support for sealably engaging a peripheral zone of said second face;

a holding support for holding said measuring electrode in contact with said central zone of said first face; and means co-acting between said holding support and said tubular support for urging said measuring electrode against only said central zone of said first face and said peripheral zone of said second face against said annular seat, thereby simultaneously providing a releasably sealed connection between said tablet and said tubular support and an electrical contact between said central zone of said first face and said measuring electrode within said gaseous atmosphere the contact between said measuring electrode and said central zone being the sole area where pressure is transmitted between the holding support and the first surface of the tablet.

2. The probe of claim 1, wherein said holding support comprises a tubular casing enclosing said tubular support and a cap removably affixed to an end of said casing nearest to said measuring head, said measuring electrode being secured to said cap.

3. The probe of claim 2, further comprising gasket means disposed between said casing and said tubular support, said cap including apertures affording communication between said gaseous atmosphere and the interior of said casing. electrode to press said tablet against said seal.

4. The probe of claim 2, further comprising means electrically connecting said casing to said measuring electrode.

5. The probe of claim 4, wherein said casing is lined with a layer of platinum.

6. The probe of claim 1, wherein said seat surface of said tubular support is a plane, annular shoulder, and wherein a washer comprising a platinum ring is disposed between said table and said shoulder.

7. The probe of claim 1, wherein said measuring electrode comprises a supporting portion and a platinum wire wound about said supporting portion.

8. The probe of claim 1, further comprising two wires joined at a soldered junction to form a thermocouple constituting said reference electrode, said two wires constituting means for transmitting through said probe a potential from said reference electrode and a potential difference from said thermocouple.

9. The probe of claim 8, wherein said first face of said tablet is plane and said second face of said tablet is parallel to said first face and includes a hollow, said soldered junction and adjoining portions of said two wires being crumpled into a ball and accommodated in said hollow, said probe further comprises means for maintaining said ball of wire in contact with said second face of said tablet at a plurality of points.

10. The probe of claim 8, further comprising a tubular conduit of insulating material fitted within said tubular support and including at the end of said conduit remote from said measuring head a connection pipe, said two wires of said thermocouple constituting said reference electrode being guided within said conduit, and said connection pipe being. adapted to admit into said conduit a flow of said reference atmosphere for sweeping said second face of said tablet of solid electrolyte.

11. A probe according to claim 1, further comprising spring means disposed between said tubular casing and said tubular support, said tubular casing and support being axially movable with respect to each other, such that said measuring electrode is urged against said first face and said peripheral zone of said second face is urged against said seat by said spring means.

12. A probe according to claim 1, wherein each of said measuring and reference electrodes comprises a plurality of point contacts which contact a plurality of points of the central zones of the corresponding faces of said tablet.

13. A probe according to claim 12, wherein said measuring electrode further comprises a rigid body having a front portion disposed toward said first face, said front portion comprising a network of projections which serve as said plurality of point contacts, while simultaneously allowing circulation of said gaseous atmosphere between and among said projections and said first face.

14. A probe according to claim 1, wherein said holding support and said tubular support are comprised of a refractory material different from the material of said solid electrolyte, and wherein said electrodes are comprised of platinum.

* * * * *